(12) United States Patent
Jakob

(10) Patent No.: US 8,470,227 B2
(45) Date of Patent: Jun. 25, 2013

(54) METHOD FOR THE PRODUCTION OF A PLASTIC PRODUCT HAVING A HARD PLASTIC COMPONENT AND A SOFT PLASTIC COMPONENT, AND PLASTIC PRODUCT PRODUCED USING SAID METHOD

(75) Inventor: Thomas Jakob, Selb (DE)

(73) Assignee: Raqumedic AG, Munchberg (DE)

( * ) Notice: Subject to any disclaimer, the term of this patent is extended or adjusted under 35 U.S.C. 154(b) by 0 days.

(21) Appl. No.: 12/600,423

(22) PCT Filed: Apr. 12, 2008

(86) PCT No.: PCT/EP2008/002915
§ 371 (c)(1),
(2), (4) Date: Nov. 16, 2009

(87) PCT Pub. No.: WO2008/138442
PCT Pub. Date: Nov. 20, 2008

(65) Prior Publication Data
US 2010/0152678 A1    Jun. 17, 2010

(30) Foreign Application Priority Data
May 16, 2007  (DE) .......................... 10 2007 023 129

(51) Int. Cl.
*B29C 45/16* (2006.01)
(52) U.S. Cl.
USPC .......................................... 264/255; 264/259
(58) Field of Classification Search
USPC ................................................ 264/255, 259
See application file for complete search history.

(56) References Cited

U.S. PATENT DOCUMENTS

| | | | |
|---|---|---|---|
| 4,682,703 A | | 7/1987 | Kasai et al. |
| 5,033,476 A | | 7/1991 | Kasai |
| 5,069,670 A | | 12/1991 | Vetter et al. |
| 5,147,328 A | * | 9/1992 | Dragosits et al. .............. 604/218 |
| 5,167,647 A | * | 12/1992 | Wijkamp et al. .............. 604/532 |
| 5,728,168 A | * | 3/1998 | Laghi et al. ..................... 623/36 |
| 6,068,622 A | * | 5/2000 | Sater et al. ..................... 604/524 |
| 6,575,959 B1 | * | 6/2003 | Sarge et al. ..................... 604/533 |
| 6,752,950 B2 | * | 6/2004 | Clarke ........................... 264/255 |
| 2004/0017051 A1 | | 1/2004 | Lach et al. |
| 2006/0089602 A1 | | 4/2006 | Boucherie |
| 2006/0111485 A1 | * | 5/2006 | Laghi ............................. 524/115 |
| 2009/0008966 A1 | | 1/2009 | Hebauer et al. |

FOREIGN PATENT DOCUMENTS

| | | |
|---|---|---|
| DE | 1854950 U | 7/1962 |
| DE | 1491743 A1 | 6/1969 |
| DE | 4036361 A1 | 7/1991 |
| DE | 3686347 T2 | 3/1993 |
| DE | 3750585 T2 | 4/1995 |

(Continued)

*Primary Examiner* — Jill Heitbrink
(74) *Attorney, Agent, or Firm* — Browdy & Neimark, PLLC

(57) ABSTRACT

A plastic product having a hard plastic component and a soft plastic component that adheres to the hard plastic component via at least one boundary surface is produced as follows: initially the soft component is injection molded in an injection molding die. Then the hard component is injection molded. In the plastic product produced in this manner, the soft component is surrounded over at least part of the circumference thereof by the hard component in the circumferential direction about a main demolding direction of the injection molding die. The result is a plastic product, wherein the shape and arrangement of the soft component can be tailored to functional requirements more flexibly.

9 Claims, 1 Drawing Sheet

FOREIGN PATENT DOCUMENTS

| | | |
|---|---|---|
| DE | 29602173 U1 | 6/1997 |
| DE | 10254912 B3 | 9/2004 |
| DE | 10327769 A1 | 2/2005 |
| EP | 0397977 A | 11/1990 |
| EP | 1422040 A1 | 5/2004 |
| JP | 60-912 * | 1/1985 |
| WO | 2006058515 A1 | 6/2006 |

* cited by examiner

METHOD FOR THE PRODUCTION OF A PLASTIC PRODUCT HAVING A HARD PLASTIC COMPONENT AND A SOFT PLASTIC COMPONENT, AND PLASTIC PRODUCT PRODUCED USING SAID METHOD

FIELD OF THE INVENTION

The invention relates to a method for the production of a plastic product, especially an injection needle, having a hard plastic component and a soft plastic component that adheres to the hard plastic component via at least one boundary surface. The invention furthermore relates to a plastic product produced using such a method.

BACKGROUND OF THE INVENTION

Two-component plastic products of this type are known in many different embodiments from the prior art of US 2004/0017051 A1, of DE 296 02 173 U1, of DE 14 91 743 A1, of EP 0 397 977 A and of US 2006/089602 A1. The soft component often serves as a sealing element, or for improving the tactile qualities of a hard component main body of the plastic product, for example as a handle element, such as in a toothbrush. Furthermore, plastic products are known in which a hard component is subsequently joined to a soft functional component for sealing, connecting, damping, or improving the tactile qualities. Such a subsequent joining, as a rule, adds time and expense.

SUMMARY OF THE INVENTION

It is therefore an object of the present invention to improve a plastic product of the type mentioned at the outset, in such a way that the soft component can be more flexibly tailored in its shape and arrangement to functional requirements.

This object is achieved according to the invention with a production method for the plastic product, comprising the steps of injection molding of the soft component in an injection molding die and injection molding of the hard component in the injection molding die following the injection molding of the soft component, wherein prior to the injection molding of the soft component an insert component is inserted into the injection molding die that is coated by injection molding at least in some sections thereof with the soft component and over at least part of the circumference thereof.

According to the invention it has been recognized that it is not imperative in the production of a multi-component plastic product to mold the hard component first, but that it is surprisingly also possible to start with the molding of the soft component. The injection molding of the hard component can easily be controlled in a way so that the soft component is not deformed in an undesired manner by the injected hard component. Because of the soft component/hard component order in the injection molding process, new possibilities are created for the arrangement and shaping of the soft component, without putting extra effort into designing the molded parts of the injection molding die. Especially with the design of the inventive method being such that the injection molding of the hard component and the injection molding of the soft component take place in one and the same injection molding die, the inventive method is simplified and shortened. The soft component can now be injection molded at positions within the hard component that would not be accessible with the reverse order, i.e. hard component/soft component. The two plastic components reliably adhere to each other via the boundary surface, resulting in a sturdy composite plastic product in which the two plastic components can fulfill their respective functions. The hard component imparts strength and stiffness to the plastic product. Additionally, the hard component can, optionally with additional components or within the framework of an automated assembly, constitute an assembly aid. Additionally, an insert component is inserted into the injection molding die prior to the injection molding of the soft component. In such a method, after injection molding of the soft component, the same fits closely against the insert component with good adhesion, such that, for example, a gluing of the soft component can be dispensed with.

It is an additional object of the invention to provide a plastic product in which the advantages of the inventive method are applied particularly effectively.

This object is achieved according to the invention by a plastic product that is produced in one and the same injection mold, having a hard plastic component and a soft plastic component that adheres to the hard plastic component via at least one boundary surface and having an insert component, the soft component being surrounded over at least part of the circumference thereof by the hard component in the circumferential direction about a main demolding direction of the injection molding die, being produced in the injection molding die according to a method according to the invention, wherein the insert component is coated with the soft component by injection molding at least in some sections thereof and over at least part of the circumference thereof. If, according to such a plastic product, the soft component is surrounded by the hard component in the circumferential direction about a main demolding direction of the injection molding die, it is possible, because of the soft component/hard component injection molding order to nevertheless produce both components by injection molding.

This object is further achieved according to the invention by a plastic product that is produced in one and the same injection mold, having a hard plastic component and a soft plastic component that adheres to the hard plastic component via at least one boundary surface, the soft component being surrounded over at least part of the circumference thereof by the hard component in the circumferential direction about a main demolding direction of an injection molding die, being produced according to a method comprising the steps of injection molding of the soft component in an injection molding die and injection molding of the hard component in the injection die following the injection molding of the soft component, wherein the soft component is produced of a thermoplastic elastomer, and wherein the thermoplastic elastomer has a shore hardness in the range of A5 to D70.

A hardness range of the soft component in the range of A5 to D70, especially in the range of A30 to A70, permits, in particular, a soft component that has a good sealing function.

The hard component being produced of a thermoplastic or polypropylene and the soft component being produced of cross-linked TPE (TPE-V) or a thermoplastic elastomer on styrene basis (TPE-S) have proven particularly suitable for producing an inventive plastic product having two components. In lieu of a thermoplastic elastomer it is also possible to use a silicone as the soft component. A thermoplastic elastomer according to claim 3 and a thermoplastic according to claim 4 adhere well to each other. Besides TPE-V and TPE-S, the following thermoplastic elastomers can be used for the soft component as well: TPE-A (amide basis), TPE-U (urethane basis), TPE-E (ether or ester basis) and TPE-O (olefin basis). As the styrene basis, particularly SBS (styrene-butadiene-styrene block copolymers), SEBS (styrene-ethylene-butadiene-styrene copolymers) and SIS (styrene-isoprenestyrene copolymers) can be used. Because of the good adhesion, preferred material combinations that are used are especially polypropylenes in the form of homo propylene, block propylene or random polypropylene as the hard component, and thermoplastic elastomers on styrene basis, olefin basis, and cross-linked thermoplastic elastomers as the soft component. Such material combinations result in a good bond strength and can additionally be produced economically.

In a plastic product being a medical implement, the advantages of the inventive injection molding order are applied particularly effectively, since, in particular, additional adhesives can be dispensed with, thereby simplifying the production of a medically harmless plastic product.

In an injection needle having a plastic connecting element on the hard plastic component for connecting to a syringe container, which may be designed in the form of a luer-type needle, for example, the soft component provides a reliable seal between an injection cannula designed in the form of an insert component and the hard component defining the main body.

An illustrative embodiment of the invention will be explained in more detail below, with the aid of the drawing.

DESCRIPTION OF THE PREFERRED EMBODIMENT

A luer-type needle denoted in its entirety with 1 is an example for a plastic product produced according to the invention. The luer-type needle has a steel needle 2 as the injection cannula. In a left end region 3 in FIG. 2 of the steel needle 2, which is situated opposite a free end region 4 of the steel needle 2, the steel needle 2 is surrounded over the entire circumference thereof by a soft plastic component 5. The soft plastic component 5 is TPE-V, that is a cross-linked thermoplastic elastomer. The latter has a shore hardness between A30 and A70.

Figure 1:
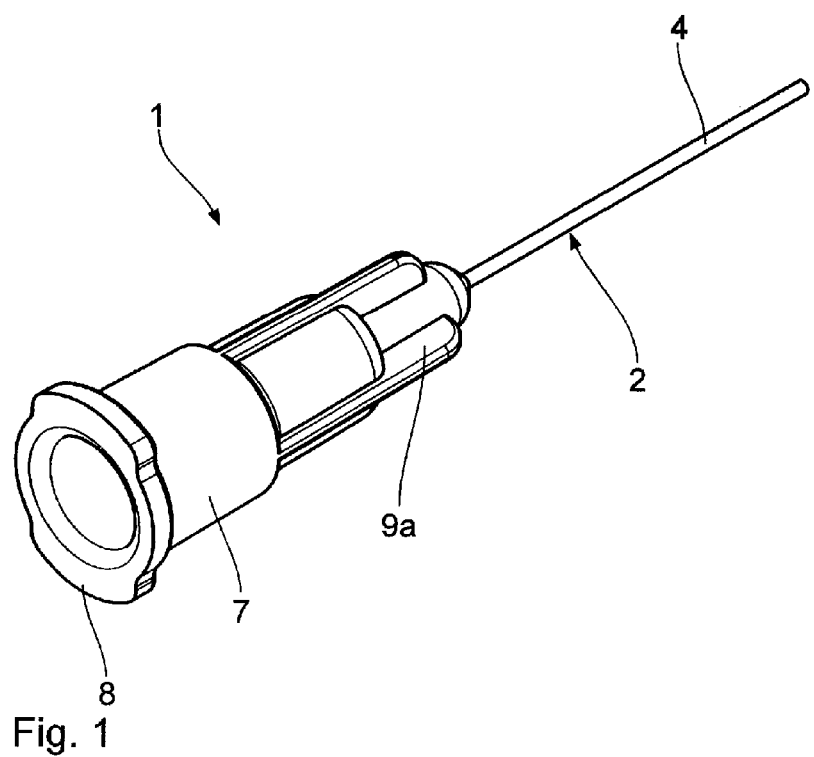
FIG. 1 shows a perspective view of a luer-type needle as an example for a plastic product produced according to the invention.
Figure 2:
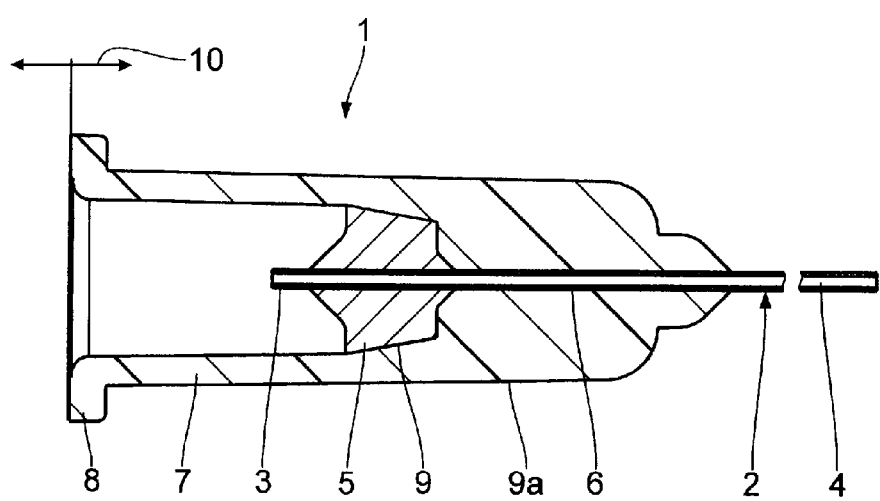
FIG. 2 shows a longitudinal section through the luer-type needle according to FIG. 1.

The soft plastic component 5, the end region 3, and a middle region 6 of the steel needle 2, which in FIG. 2, adjoins the end region to the right, are surrounded over the entire circumference thereof by a hard plastic component 7. The latter forms the main plastic body of the luer-type needle 1.

The hard plastic component 7 is shaped on the outside like it is basically known in luer-type needles, and accordingly has a standard locking collar 8 and altogether four grasping wings 9a that facilitate a rotating movement of the luer-type needle 1 about the longitudinal axis of the steel needle 2 for creating a connection of the luer-type needle 1 to a syringe container. The locking collar 8 serves as a plastic connecting element for connecting the luer-type needle 1 to the syringe container. The hard plastic component is made of polypropylene but can also be produced from a different thermoplastic.

The hard plastic component 7 adheres to the soft plastic component 5 via a boundary surface 9 that is rotation-symmetrical about the longitudinal axis of the steel needle 2. The soft plastic component 5 serves to seal the steel needle 2 with respect to the hard plastic component 7.

The luer-type needle 1 is produced as follows:

First the steel needle 2 is inserted as an insert into a not depicted injection molding die. Then the soft plastic component 5 is injection molded in the injection molding die. The plastified soft component in the injection molding die is injected through a tunnel gate. After injecting and hardening of the soft component 5, die halves that bound the shape of the soft plastic component 5 are separated along the main demolding direction 10. The soft plastic component 5 is undercut-free with respect to this main demolding direction 10.

Following the injection molding of the soft plastic component 5, the hard plastic component 7 is injection molded. The plastified hard component in the injection molding die is injected through an additional tunnel gate. The injection molding of the hard component 7 takes place only after the soft component 5 has hardened to a degree that an undesired deformation of the soft component 5 by the injected hard component 7 is prevented. The hard component 7 is injection-molded around the steel needle 2 in some sections thereof and around the soft plastic component 5.

After injection molding and hardening of the hard component 7 the injection molding dies that bound the shape of the hard plastic component 7 are likewise separated from each other along the main demolding direction 10. The hard component 7 likewise is free of undercuts along the main demolding direction 10.

The hard component 7 that is injection molded onto the soft component 5 via the boundary surface 9 adhesively adheres to the soft component 5. Additionally, both the soft component 5 and the hard component 7 adhesively adhere to the steel needle 2. The need for the use of an additional adhesive is eliminated.

The soft component 5 is surrounded by the hard component 7 over the entire circumference thereof in the circumferential direction about the main demolding direction 10, which coincides with the longitudinal axis of the steel needle 2.

The invention claimed is:

1. A method for producing a medical implement comprising a needle and having an exterior hard plastic component (7) and an interior soft plastic component (5) which is integral with and adheres to the hard plastic component (7), comprising providing an injection molding die comprising first die parts adapted to and capable of forming a first shape;
inserting a needle into and through the first die parts;
injection molding a soft plastic in contact with the needle and to form the soft plastic component (5) in the shape of said first die parts around the needle, the soft plastic component (5) having a first length;
at least partly solidifying said soft plastic of the soft plastic component (5) and separating said first die parts;
injection molding a hard plastic into the injection molding die and over and in contact with both the soft plastic component (5) and the needle, and adhering the hard plastic to the soft plastic by action of the injection molding;
hardening the hard plastic to form the hard plastic component (7) in contact with and adhered to the soft plastic component, the hard plastic component (7) having a second length longer than the first length, and separating the resultant medical implement from the injection molding die;
wherein the medical implement is an injection needle.

2. The method of claim 1 wherein the soft plastic is a thermoplastic elastomer having a shore hardness of A5-D70, and the hard plastic is a propylene polymer.

3. The method of claim 2 wherein the thermoplastic elastomer has a shore hardness in the range of A30 to A70.

4. The method of claim 1 wherein the hard plastic component comprises a thermoplastic.

5. The method of claim 4 wherein the thermoplastic is polypropylene.

6. The method according to claim 1 wherein the soft component (5) comprises a cross-linked TPE.

7. The method of claim 6, wherein the soft component (5) comprises TPE-V.

8. The method of claim 1 wherein the soft component (5) comprises a thermoplastic elastomer based on styrene.

9. The method of claim 8, wherein the soft component (5) comprises TPE-S.

\* \* \* \* \*

UNITED STATES PATENT AND TRADEMARK OFFICE
CERTIFICATE OF CORRECTION

PATENT NO.       : 8,470,227 B2                                  Page 1 of 1
APPLICATION NO.  : 12/600423
DATED            : June 25, 2013
INVENTOR(S)      : Jakob It is certified that error appears in the above-identified patent and that said Letters Patent is hereby corrected as shown below:

On the Title Page:

At item (73) Assignee, correct the incorrect assignee name by deleting "Raqumedic AG" and inserting --Raumedic AG--.

Signed and Sealed this
Tenth Day of September, 2013

Teresa Stanek Rea
*Acting Director of the United States Patent and Trademark Office*